US007876876B2

(12) United States Patent
Ohta et al.

(10) Patent No.: US 7,876,876 B2
(45) Date of Patent: Jan. 25, 2011

(54) RADIATION IMAGE CAPTURING APPARATUS

(75) Inventors: Yasunori Ohta, Yokohama (JP);
Kuniaki Miyako, Minami-ashigara (JP);
Kazuo Hakamata, Odawara (JP);
Hajime Nakata, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/236,685

(22) Filed: Sep. 24, 2008

(65) Prior Publication Data

US 2009/0080606 A1    Mar. 26, 2009

(30) Foreign Application Priority Data

Sep. 25, 2007    (JP) .............................. 2007-246782

(51) Int. Cl.
*A61B 6/04* (2006.01)

(52) U.S. Cl. ......................................................... 378/37

(58) Field of Classification Search .................... 378/37
See application file for complete search history.

(56) References Cited

U.S. PATENT DOCUMENTS 6,268,614 B1    7/2001    Imai
6,463,122 B1 *  10/2002   Moore .......................... 378/37
7,200,199 B2 *  4/2007    Andreasson et al. .......... 378/37
7,319,734 B2 *  1/2008    Besson et al. ................. 378/37
2005/0036584 A1 * 2/2005  Lebovic et al. ................ 378/37
2005/0254620 A1 * 11/2005 Shoji et al. .................... 378/37

FOREIGN PATENT DOCUMENTS

JP    2000-037374 A    2/2000

* cited by examiner

*Primary Examiner*—Chih-Cheng G Kao
(74) *Attorney, Agent, or Firm*—Sughrue Mion, PLLC

(57) ABSTRACT

A radiation image capturing apparatus includes a housing for housing a radiation detector. The housing has a wall inclined with respect to a detection surface of the radiation detector, and the wall defines a space inclined with respect to the detection surface. The space allows heat transfer medium such as air of relatively high temperatures (higher than that of outside air, for example) to rise along a slope defined by the space. If the region around the detection surface is heated to high temperatures, airflow is generated within the space, forcing the relatively high-temperature heat transfer medium away from the vicinity of the radiation detector, thereby allowing the whole radiation detector to be cooled in a uniform manner.

5 Claims, 6 Drawing Sheets

RADIATION IMAGE CAPTURING APPARATUS

BACKGROUND OF THE INVENTION

1. Field of the Invention

The present invention relates to a radiation image capturing apparatus that includes a radiation detector for detecting a radiation image of a subject and generating electrical signals corresponding to the detected radiation image, and more particularly, to a radiation image capturing apparatus that includes a mechanism for cooling the radiation detector.

2. Description of the Related Art

In a radiation image capturing apparatus, such as an X-ray breast image capturing apparatus (e.g., mammography apparatus) or the like, a radiation image is generated by exposing a subject (patient) to radiation and recorded into a radiation image recording unit (i.e., a radiation detector). The radiation image recording unit is thereafter scanned with reading light emitted from a reading light source moved relative to the radiation image recording unit to allow readout of the information associated with the recorded radiation image. An example of such a radiation image capturing apparatus is disclosed in U.S. Pat. No. 6,268,614.

Examples of the radiation image recording unit that can be used in the above-mentioned apparatus include a radiation detector of electric readout type having a plurality of photoelectric conversion elements and devices such as thin-film transistors (TFT), CCD (Charge Coupled Device) or CMOS (Complementary Metal Oxide Semiconductor) sensor, or a radiation detector of light readout type, direct conversion type, or indirect conversion type.

In such radiation image capturing apparatuses, it is necessary to maintain a proper temperature range because of constraints resulting from the temperature characteristics of the photoelectric conversion elements, the effects of thermal noise generated by the electrical circuit, and the like. Therefore, a radiation image capturing apparatus is provided with an air or water-type cooler. One example of such an apparatus is disclosed in Japanese Laid-Open Patent Publication No. 2000-037374.

The radiation image capturing apparatus disclosed in Japanese Laid-Open Patent Publication No. 2000-037374 is directed to effective cooling of the radiation detector. The radiation image capturing apparatus disclosed in the above-mentioned publication includes, as can be seen in FIG. 1 of the publication, a two-dimensional radiation detector 5 and a signal converter 6 contained in a housing 4 of an image capturing unit 3 in this order from the front of the housing 4. An upper portion of the housing 4 is provided with a fan 7, which serves as a cooling means, and a lower portion of the housing 4 is provided with an inlet port 4a for introducing outside air. Release of the heat generated by the two-dimensional radiation detector 5 is accomplished by actuating the fan 7 and thereby introducing air into the housing 4 through the inlet port 4a.

In the apparatus disclosed in Japanese Laid-Open Patent Publication No. 2000-037374, the inlet port 4a is formed at one end of the radiation detector 5, while the fan 7 is located at the other end, so that cooling of the whole radiation detector can be achieved. In many radiation image capturing apparatuses, however, the arrangement of the radiation detector within the image capturing unit is restricted for various reasons. The image capturing unit of a mammography apparatus, for example, is required to be movable around the breast so that images of the breast from different directions can be captured. Consequently, a large size for the image capturing unit housing is not permitted, and the radiation detector has to be contained in a small space. Further, since image capturing up to the base of the breast is required, the radiation detector is located within the housing so that the distance between the radiation detector and the chest wall of the patient becomes suitably short during a mammography examination. Thus, the radiation detector is disposed adjacent to the front end of the housing that abuts against the chest wall of the subject. Consequently, the space between the radiation detector and the front end is narrow, and it is not possible to release sufficient heat from the radiation detector. This results in non-uniform cooling of the radiation detector, which, in turn, may reduce image capturing accuracy.

SUMMARY OF THE INVENTION

It is an object of the invention to provide a radiation image capturing apparatus capable of uniformly cooling a radiation detector as a whole irrespective of constraints on the arrangement of the radiation detector.

A radiation image capturing apparatus according to the present invention includes a radiation detector for detecting a radiation image of a subject and generating an electrical signal corresponding to the radiation image, and a housing for containing the radiation detector. The housing includes a wall inclined with respect to a detection surface of the radiation detector and defining a space inclined with respect to the detection surface.

According to the present invention, the space formed within the housing and inclined with respect to the detection surface of the radiation detector allows air (heat transfer medium) of relatively high temperatures (higher than that of outside air, for example) to rise along a slope defined by the space. If the region around the detection surface is heated to high temperatures, airflow is generated within the space, forcing the relatively high-temperature air away from the vicinity of the radiation detector, thereby allowing the whole radiation detector to be cooled in a uniform manner.

Preferably, the housing includes an inlet channel formed at a level lower than the space in order to introduce outside air into the space, and an outlet channel formed at a level higher than the space in order to discharge the air that has passed through the space. The relatively high-temperature air rises within the housing and is discharged to the outside of the housing through the outlet channel, due to the relation with the outside air. The airflow cools the housing with a simple configuration.

The radiation image capturing apparatus may comprise a mammography apparatus.

If the radiation image capturing apparatus according to the invention is a mammography apparatus, the wall is preferably inclined upwardly in a direction away from a front end of the housing that abuts against a chest wall of the subject. Thus, the relatively high-temperature air can be moved away from the subject and the detection surface of the radiation detector with a simple configuration.

The wall, which is inclined upwardly in the direction away from the front end of the housing, may include a curved portion. The wall may also include a flat portion facing the radiation detector in addition to the curved portion. Then, only the flat portion faces the radiation detector, and the curved portion does not face the radiation detector.

Preferably, the housing is rotatable with respect to a base about a horizontal shaft, and the housing comprises a circumference that includes part of the wall. Also, an upper side of the circumference is inclined upwardly in the direction away from the front end of the housing irrespective of the rotational orientation of the housing. This arrangement allows mammography apparatuses, which are capable of adjusting the angular orientation of the radiation detector by rotation with respect to the base, to achieve reliable cooling of the radiation detector constantly, since the relatively high-temperature air can move upwardly irrespective of the rotational orientation of the radiation detector.

The circumference of the housing is preferably provided with a plurality of outlets formed in a base side thereof. These slits allow smooth discharge of the relatively high-temperature air regardless of the rotational orientation of the housing with respect to the base.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Figure 1:
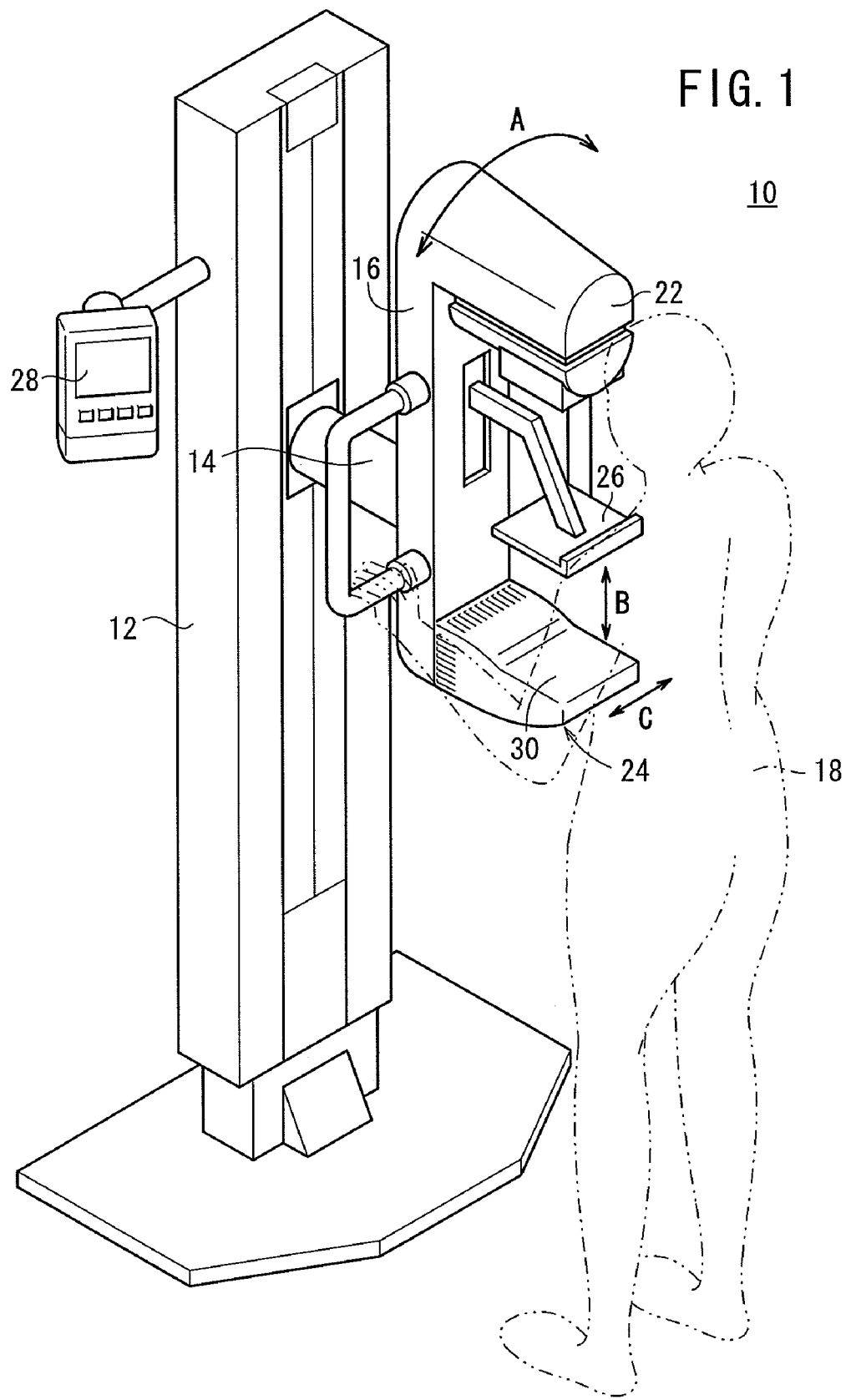
FIG. 1 is a perspective view of a mammography apparatus embodying a radiation image capturing apparatus according to an embodiment of the present invention.

FIG. 1 shows a perspective view of a mammography apparatus 10 for breast cancer screening or the like, which is a radiation image capturing apparatus according to an embodiment of the present invention.

The mammography apparatus 10 includes an upstanding base 12, an arm 16 fixed to a pivot shaft 14 that is connected substantially centrally to the base 12, a radiation source housing unit 22 fixed to one end of the arm 16 and housing a radiation source (not shown) for applying radiation X (electromagnetic waves for recording, see FIG. 2) to a breast 20 (see FIG. 2) which is the image capturing site of a subject 18, an image capturing base 24 fixed to the other end of the arm 16 so as to oppose to the radiation source housing unit 22, and a compression plate 26 for holding the breast 20 by compressing it against the image capturing base 24.

The arm 16 holding the radiation source housing unit 22 and the image capturing base 24 can be rotated about the pivot shaft 14 in the directions indicated by double-headed arrow A to adjust the image capturing direction of the breast 20 of the subject 18. The compression plate 26 is connected to the arm 16 between the radiation source housing unit 22 and the image capturing base 24 so as to be movable in the directions shown by double-headed arrow B.

The base 12 is also provided with a display control panel 28 for displaying image capturing information obtained with the mammography apparatus 10 and the identification (ID) information or the like of the subject 18. The image capturing information includes the image capturing site, image capturing direction, or the like of the subject 18. The display control panel 28 also allows settings of the above-mentioned information, if desired.

Figure 2:
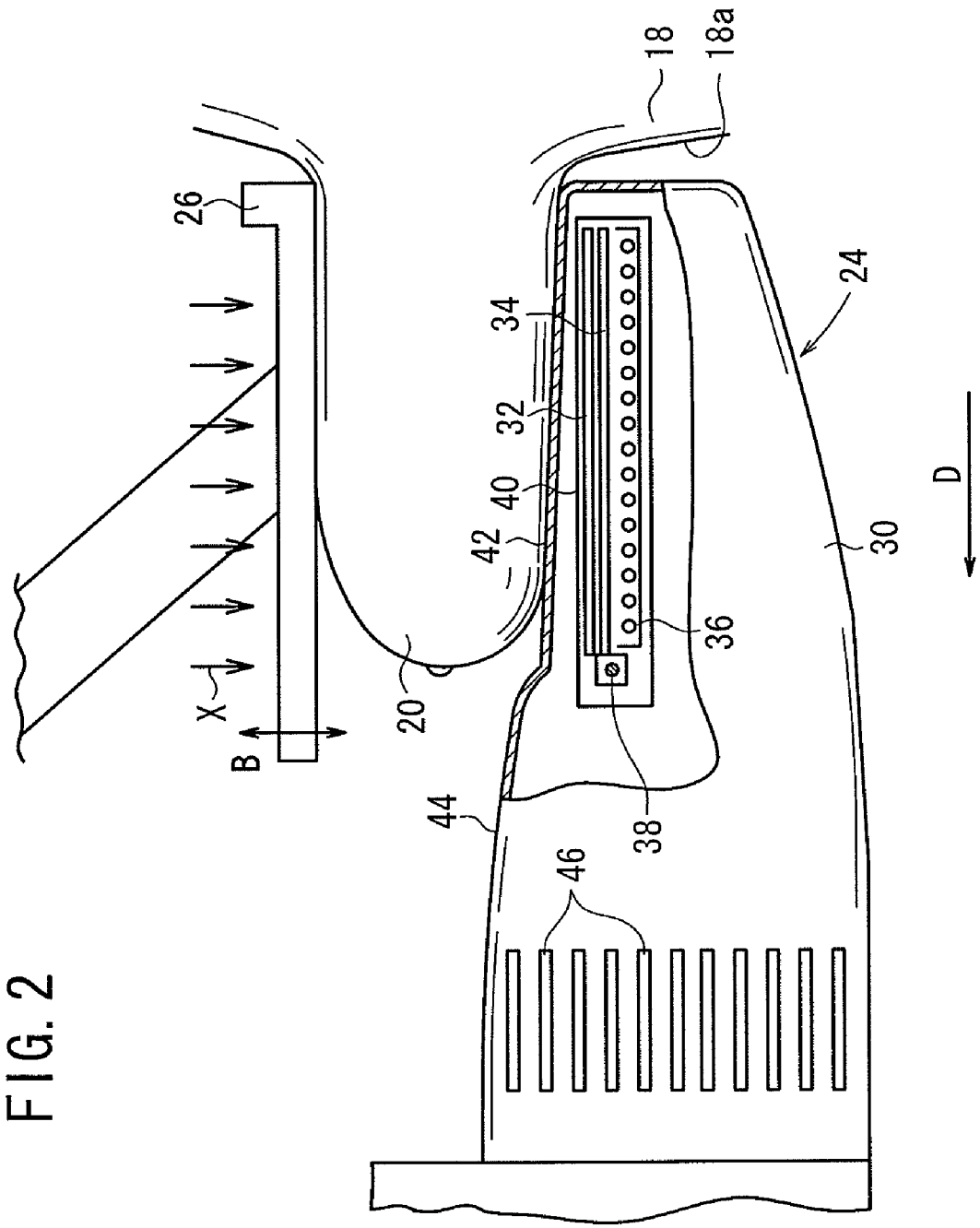
FIG. 2 is a partially cross-sectional side view of a main part of the mammography apparatus of FIG. 1, including the image capturing base and showing the internal structure thereof.

FIG. 2 is a partially cross-sectional view of a main part of the mammography apparatus 10, showing the internal structure of the image capturing base 24. FIG. 2 shows the breast 20, i.e., the image capturing site of the subject 18, being placed between the image capturing base 24 and the compression plate 26.

Contained within a housing 30 of the image capturing base 24 is a planar radiation detector 32. The radiation detector 32 stores radiation image information captured based on the radiation X emitted from the radiation source in the radiation source housing unit 22 and generates electric signals corresponding to the radiation image information. Also contained within the housing 30 is a reading light source 34 that applies linear reading light onto the radiation detector 32 in order to read out the recorded radiation image information stored in the radiation detector 32. Further disposed within the housing 30 is an erasing light source 36 that applies erasing light onto the radiation detector 32. The reading light source 34 may be moved with a scanning mechanism 38 in the direction perpendicular to the plane of FIG. 2 (in the direction indicated by arrow C in FIG. 1) so that the reading light is scanned over the radiation detector 32.

As shown in FIG. 2, the housing 30 has a first inclined wall 42 facing a detection surface 40 of the radiation detector 32 and a second inclined wall 44 formed on the pivot shaft 14 side of the housing 30. The first inclined wall 42 is a straight (flat) wall that is inclined upwardly in a direction away from a front end of the housing 30, which abuts against a chest wall 18a of the subject 18 (i.e., in a direction indicated by the arrow D in FIG. 2). The second inclined wall 44 is a curved wall also inclined upwardly in the direction away from the front end of the housing 30. The first and second inclined walls 42 and 44 thus define a space that is inclined with respect to the detection surface 40 of the radiation detector 32.

Figure 3B:
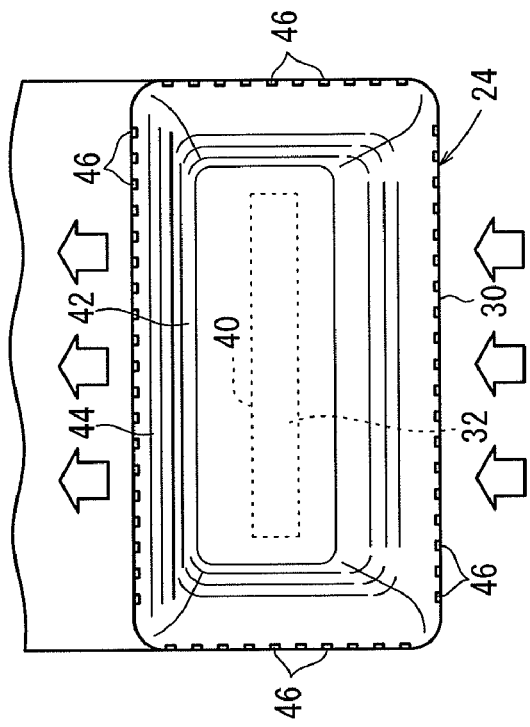
FIG. 3B is a front view of the image capturing base of FIG. 2, showing the airflow therein.
Figure 4B:
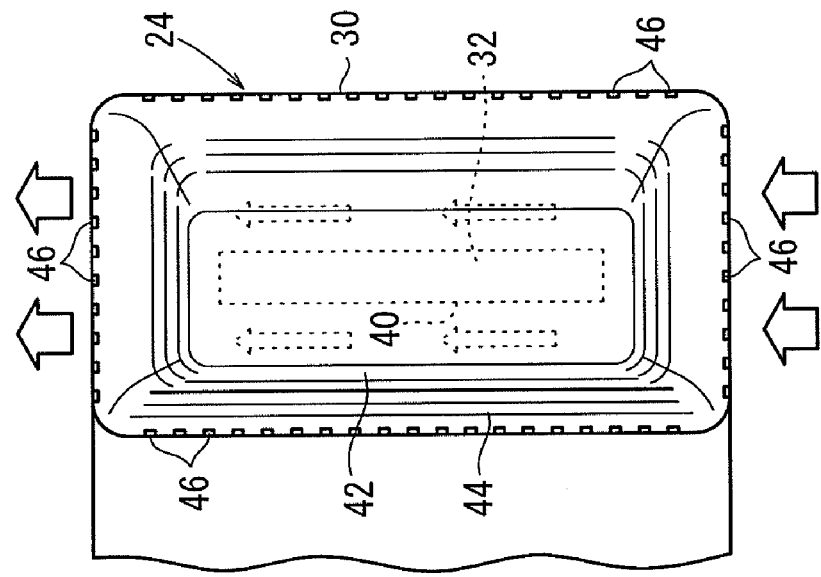
FIG. 4B is a front view of the image capturing base of FIG. 2 rotated 90 degrees, showing the airflow therein.
Figure 4A:
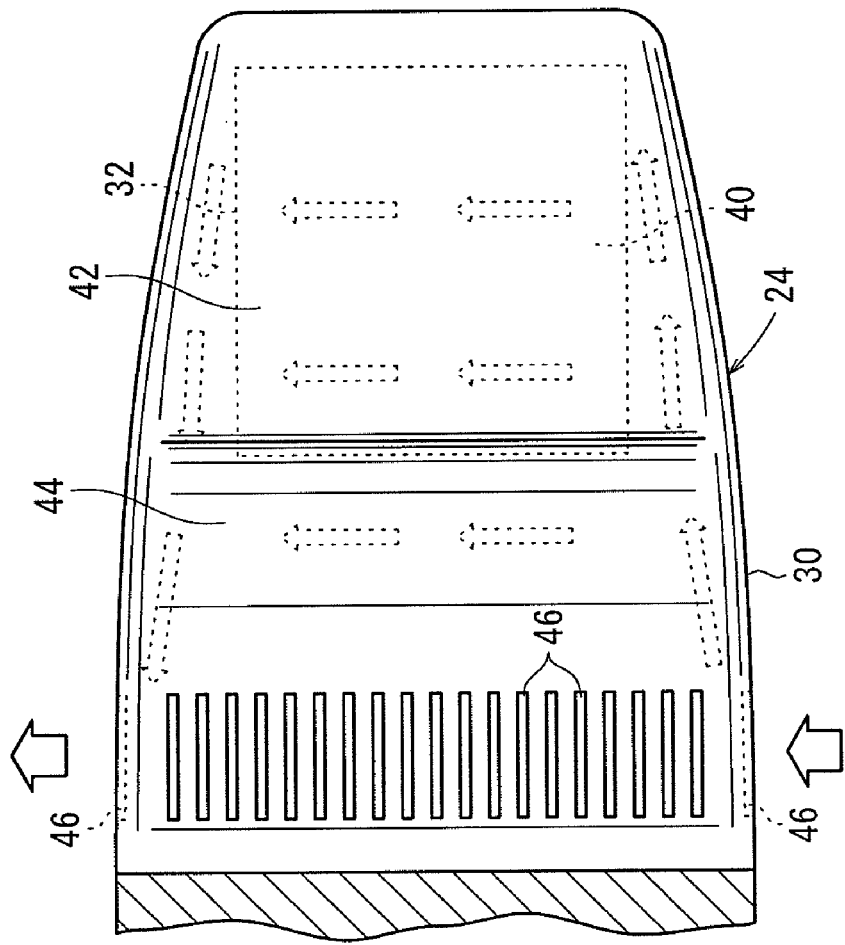
FIG. 4A is a side view of the image capturing base of FIG. 2 rotated 90 degrees, showing the airflow therein.

The walls of the housing 30 other than the first and second inclined walls 42 and 44, i.e., (assuming that the first and second inclined walls 42 and 44 are formed on an upper wall of the housing 30) right and left sidewalls and a lower wall are formed so that the width between opposing walls increases with distance from the front end of the housing 30 (see FIGS. 3B, 4A, and 4B). The upper and lower walls and the right and left sidewalls of the housing 30 thus define a space, wherein the distance from each wall to a plane including the radiation detector 32 gradually increases towards the pivot shaft 14.

The housing 30 is further provided with a plurality of slits 46 formed successively around the circumference of the housing 30 on the side of the pivot shaft 14.

The radiation detector 32 is a direct-conversion, light readout type solid-state detector. The radiation detector stores radiation image information produced based on the radiation X that has passed through the breast 20 as an electrostatic latent image. Further, the radiation detector 32 generates an electric current corresponding to the amount of electric charge of the electrostatic latent image, when scanned by the reading light from the reading light source 34. An example of the radiation detector 32 that may be utilized in the present embodiment is disclosed in U.S. Pat. No. 6,268,614.

The operation of the mammography apparatus 10 according to the present embodiment and configured as above will now be described.

First, ID information of the subject 18, image capturing conditions, and the like are provided to the mammography apparatus 10 through a console (not shown), an ID card, or the like. The ID information may include the name, age, gender, or the like of the subject 18 and can be acquired from an ID card of the subject 18. If the mammography apparatus 10 is connected to a network, the ID information may also be acquired from other apparatuses on the network. The image capturing conditions may include the image capturing site, the image capturing direction, and the like specified by the physician. These items of information may be acquired from a higher-level apparatus on the network or entered through the console by a radiologist. The ID information, image capturing conditions, or the like may be displayed on the display control panel 28 of the mammography apparatus 10 for verification.

The radiologist then sets the mammography apparatus 10 according to the specified image capturing conditions. The image capturing direction of the breast 20 may include, for example, a craniocaudal view (CC), a mediolateral view (ML), and a mediolateral oblique view (MLO), in which image capturing is performed by exposing the breast 20 to the x-rays from the top, side, and an oblique angle, respectively. The arm 16 is rotated about the pivot shaft 14 in accordance with the specified image capturing direction.

Next, the breast 20 of the subject 18 is positioned with respect to the mammography apparatus 10, i.e., the breast 20 is placed on the image capturing base 24 and the compression plate 26 is moved down to hold the breast 20 between the image capturing base 24 and the compression plate 26 (see FIG. 2).

After the above preparatory operation has been completed, the radiation source (not shown) in the radiation source housing unit 22 is activated to expose the breast 20 to radiation X in accordance with the predetermined image capturing conditions. The radiation X that has passed through the breast 20 negatively charges the radiation detector 32 to form a latent image thereon. Negative charging of the radiation detector 32 may be achieved in accordance with the method disclosed in U.S. Pat. No. 6,268,614, for example.

After the latent image has been recorded to radiation detector 32, the reading light source 34 (see FIG. 2) is moved by the scanning mechanism 38 in the direction indicated by arrow C of FIG. 1 (auxiliary direction) to scan the reading light emitted from the reading light source 34 on the radiation detector 32, allowing a processing circuit (not shown) to read out the radiation image information from the radiation detector 32. For further details about the readout processing, see the above-mentioned U.S. Pat. No. 6,268,614, which discloses applicable processing.

During the recording and readout of the radiation image information in/from the radiation detector 32, heat is generated from the radiation detector 32 and other devices arranged within the housing 30 of the image capturing base 24. The heat accumulates and thus the temperature increases inside the housing 30, which may result in abnormal operation of the radiation detector 32. As already mentioned, the space formed between the radiation detector 32 and the front end of the housing 30 is quite narrow, making it difficult to release the heat generated by the radiation detector 32. The present embodiment, however, achieves cooling of the interior of the housing 30, and in particular, the narrow space mentioned above in the following manner.

Figure 3A:
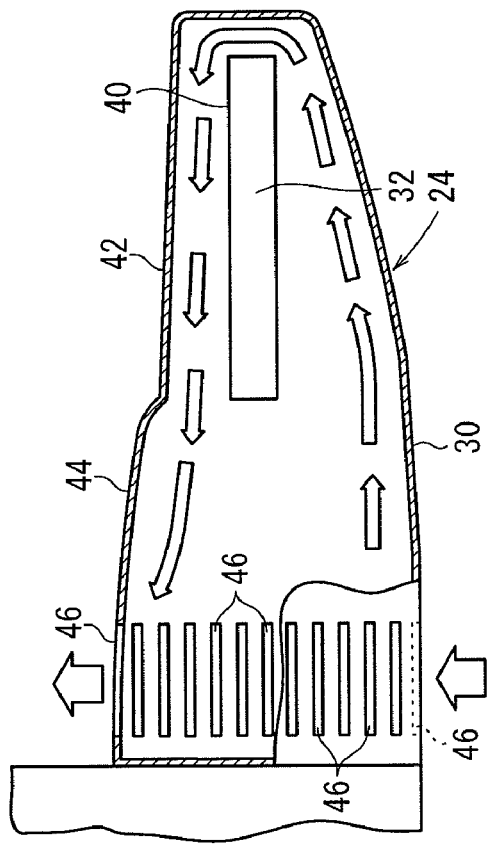
FIG. 3A is a cross-sectional side view of the image capturing base of FIG. 2, showing the airflow therein.

If the radiation detector 32 is arranged horizontally as shown in FIGS. 1, 3A, and 3B, the relatively high-temperature air around the radiation detector 32 rises as a result of being lighter than the ambient air and moves along the first and second inclined walls 42 and 44 towards the pivot shaft 14. The relatively high-temperature air then flows out through the slits 46 located on the upper side of the horizontally orientated housing 30.

The movement of the relatively high-temperature air mentioned above creates airflow in the housing 30. This airflow causes air of room temperature to be drawn into the housing 30 through the slits 46 on the lower side of the housing 30 and flow within the housing 30. A part of the drawn air flows towards the radiation detector 32, absorbs heat around the radiation detector 32 and thereby becomes warm air. The heated air rises and moves along the first and second inclined walls 42 and 44 towards the pivot shaft 14 in the manner described above.

In FIGS. 3A and 3B, the radiation detector 32 is shown in a simplified form, with components such as the reading light source 34 and the erasing light source 36 omitted for clarity. FIGS. 4A, 4B, 5A, 5B, 6A, and 6B have been simplified in the same manner.

When the arm 16 is rotated 90 degrees from the orientation shown in FIG. 1 to orientate the radiation detector 32 vertically as shown in FIGS. 4A and 4B, either the right or left sidewall is located on the upper side of the housing 30. Since the sidewalls are inclined so that they diverge from each other in a direction from the subject 18 towards the pivot shaft 14, in this case again, the relatively high-temperature air is discharged through the slits 46 on the sidewall located on the upper side of the vertically aligned housing 30 in a similar manner to that described with reference to FIGS. 3A and 3B.

As described above, the housing 30 of the present embodiment includes the first and second inclined walls 42 and 44 that are inclined with respect to the detection surface 40 of the radiation detector 32 and that define a space inclined with respect to the detection surface 40 of the radiation detector 32.

According to the present embodiment, a space is formed within the housing 30 that is inclined with respect to the detection surface 40 of the radiation detector 32, and relatively high-temperature air moves obliquely upward along this inclined space. Thus, when the air around the detection surface 40 (and in particular, the air in the narrow space formed between the radiation detector 32 and the front end of the housing 30 that abuts against the chest wall 18a of the subject 18) is heated to relatively high temperatures, airflow occurs in the inclined space, allowing the relatively high-temperature air to be removed from the vicinity of the radiation detector 32. As a result, cooling of the whole radiation detector 32 can be realized in a uniform manner.

The housing 30 introduces outside air through the slits 46 on the lower side thereof and discharges the relatively high-temperature air through the slits 46 on the upper side. The relatively high-temperature air rises and is discharged from the housing 30, and the outside air is introduced into the housing 30, allowing cooling of the inside of the housing 30 to be achieved using a simple configuration.

The first and second inclined walls 42 and 44 are inclined upwardly in the direction away from the front end of the housing 30 that abuts against the chest wall 18a of the subject 18 (i.e., in the direction of arrow D of FIG. 2). Thus, with a simple configuration, the relatively high-temperature air can be moved away from the subject 18 and the detection surface 40 of the radiation detector 32.

The housing 30 is rotatable with respect to the base 12 about the pivot shaft 14. The circumference of the housing 30 includes part of the first and second inclined walls 42 and 44. Irrespective of the rotational orientation of the housing 30, the upper side of the circumference is inclined upwardly in the direction away from the front end of the housing 30 that abuts against the chest wall 18a of the subject 18. This arrangement allows radiation image capturing apparatus, which is capable of adjusting the angular position of the radiation detector 32 by rotating it with respect to the base 12, such as the mammography apparatus 10, to achieve reliable cooling of the radiation detector 32. This is because the relatively high-temperature air can move upwardly irrespective of the rotational orientation of the radiation detector 32.

The circumference of the housing 30 is provided with the plurality of slits 46 on the base 12 side thereof. These slits 46 allow smooth discharge of the relatively high-temperature air regardless of the angular orientation of the housing 30 with respect to the base 12.

The present invention is not limited to the embodiment mentioned above. Various changes and modifications may be made in light of the description herein. For example, the invention can make use of any of the following forms.

The radiation image capturing apparatus to which the above-mentioned embodiment can be applied is not limited to the mammography apparatus 10, but may also be other types of radiation image capturing apparatus such as those that utilize electronic cassettes.

Although the above-mentioned embodiment employs the direct-conversion, light readout type radiation detector 32, a radiation detector of the indirect conversion type may be used that includes a scintillator for converging radiation X into visible light, and a photoconductive recording layer that generates electrical charge pairs when exposed to the visible light. Further, a radiation detector of the electric readout type may also be utilized.

Figure 5B:
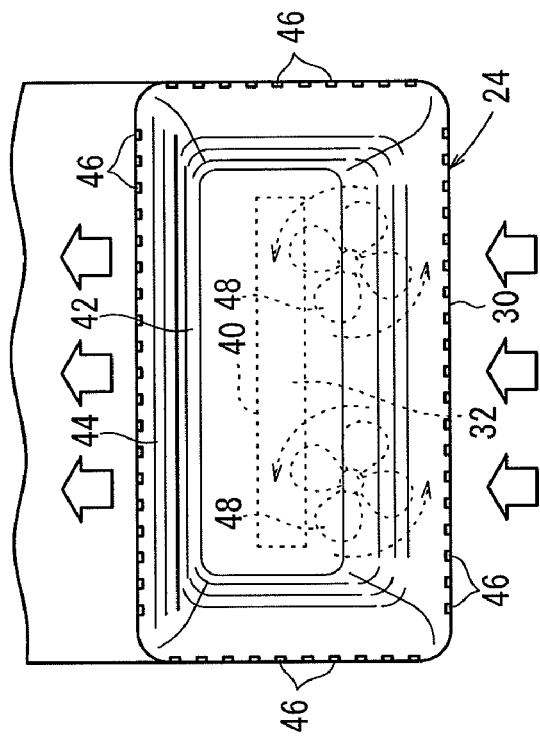
FIG. 5B is a front view of the first modification of the image capturing base, showing the airflow therein.
Figure 5A:
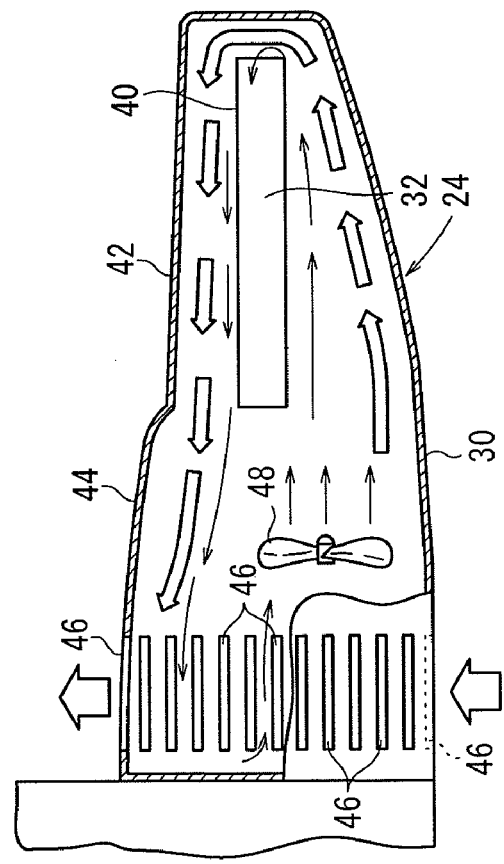
FIG. 5A is a cross-sectional side view of a first modification of the image capturing base, showing the airflow therein.

In the above-mentioned embodiment, cooling of the radiation detector 32 is realized by the airflow within the housing 30 generated by the rise of the relatively high-temperature air. The cooling of the radiation detector 32, however, may be achieved in a variety of other ways. For example, as shown in FIGS. 5A and 5B, a plurality of air circulating fans 48 may be provided within the housing 30 to force the air to flow from the lower side to the upper side of the radiation detector 32 (i.e., from the side of the radiation detector 32 opposite the detection surface 40 towards the side of the detection surface 40) in order to cool the detection surface 40. Note that the number of the air circulating fans 48 may also be one or more than two.

Figure 6A:
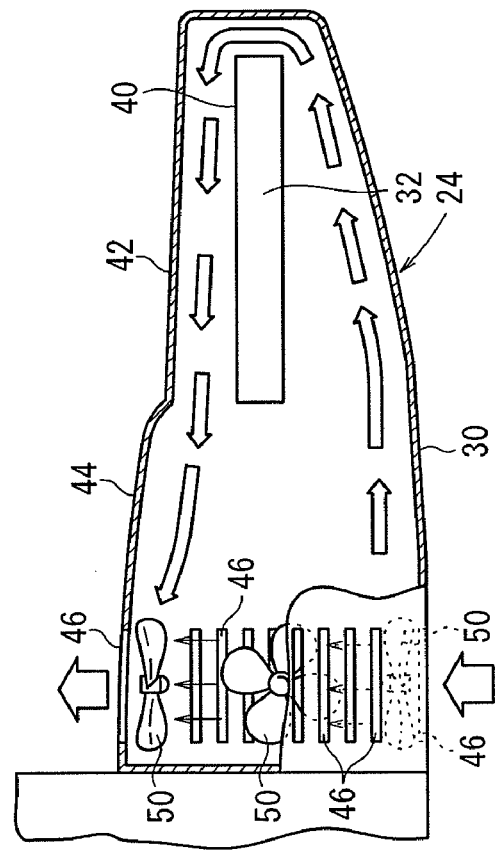
FIG. 6A is a cross-sectional side view of a second modification of the image capturing base, showing the airflow therein.
Figure 6B:
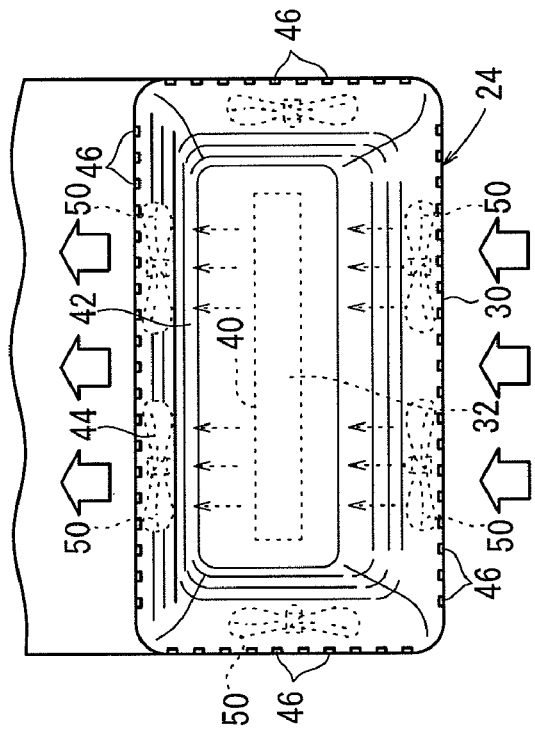
FIG. 6B is a front view of the second modification of the image capturing base, showing the airflow therein.

Alternatively, as shown in FIGS. 6A and 6B, a plurality of fans 50 may be provided to the housing 30 on the side of the pivot shaft 14, two to each of the upper and lower walls and one to each sidewall of the housing 30, so that air is forced to flow from the lower side to the upper side of the radiation detector 32 to realize cooling of the radiation detector 32. A sensor (not shown) for detecting the angular orientation of the housing 30 with respect to the base 12 may be provided in the housing 30, pivot shaft 14, or the like to determine which of the fans 50 should be actuated as an inlet or outlet fan. For example, the fans 50 determined to be located on the lower side of the housing 30 based on the output of the sensor may be actuated as inlet fans, while the fans 50 on the upper side may be actuated as outlet fans. It should be noted that the number of the fans 50 in the configuration shown in FIGS. 6A and 6B is not limited to six, and the housing 30 may be provided with one or more fans. Further, the arrangement of the fans 50 is not restricted to that shown in FIGS. 6A and 6B, and can be modified, if desired.

The housing 30 of the above-mentioned embodiment is provided with the plurality of slits 46 formed in the housing 30 on the side of the pivot shaft 14. The slits 46, however, may be replaced with other outlets such as a louver. Further, the number of slits 46 may also be altered, if desired.

In the above-mentioned embodiment, the walls of the housing 30 are formed so that the width between opposing walls increases in the direction away from the subject 18 to the pivot shaft 14. The configuration of the housing 30, however, is not limited to the above, and use of the above-described form may be limited to a part of the housing 30.

Further, the housing 30 is not limited to the shape shown in the figures, but may have a variety of other contours including a horn-like shape.

What is claimed is:

1. A mammography apparatus, comprising:
an x-ray radiation detector for detecting an x-ray radiation image of a subject and generating an electrical signal corresponding to the x-ray radiation image, and
a housing for housing the x-ray radiation detector,
a base for supporting the housing, the base having a horizontal shaft, and the housing being rotatable with respect to the base about the horizontal shaft,
wherein the housing includes a wall inclined with respect to a detection surface of the x-ray radiation detector,
wherein the wall includes an inner wall surface defining a space inclined with respect to the detection surface,
wherein the wall includes a contact surface that is positioned between a breast of the subject and the x-ray radiation detector so as to contact the breast,
wherein the inner wall surface is inclined upwardly in a direction away from a front end of the housing that abuts against a chest wall of the subject, and
wherein the housing comprises a circumference that includes part of the wall, and wherein an upper side of the circumference is inclined upwardly in a direction away from a front end of the housing irrespective of a rotational orientation of the housing, and the front end abuts against a chest wall of the subject.

2. The mammography apparatus according to claim 1, wherein the housing includes an inlet channel formed at a level lower than the space in order to introduce outside air into the space, and an outlet channel formed at a level higher than the space in order to discharge the air that has passed through the space.

3. The mammography apparatus according to claim 1, wherein the wall includes a curved portion.

4. The mammography apparatus according to claim 3, wherein the wall further includes a flat portion, only the flat portion facing the x-ray radiation detector.

5. The mammography apparatus according to claim 1, wherein the circumference of the housing is provided with a plurality of outlet openings formed in a base side of the housing.

* * * * *